(12) United States Patent
Chen et al.

(10) Patent No.: US 8,829,245 B2
(45) Date of Patent: Sep. 9, 2014

(54) 3-AMINOMETHYL-3, 5, 5-TRIMETHYL CYCLOHEXYLAMINE PREPARATION METHOD

(75) Inventors: Changsheng Chen, Yantai Shandong (CN); Yuan Li, Yantai Shandong (CN); Wenjuan Zhao, Yantai Shandong (CN); Hongyin Cui, Yantai Shandong (CN); Weiqi Hua, Yantai Shandong (CN)

(73) Assignees: Wanhua Chemical Group Co., Ltd., Yantai, Shandong (CN); Wanhua Chemical (Ningbo) Co., Ltd., Ningbo, Zhejiang (CN)

( * ) Notice: Subject to any disclaimer, the term of this patent is extended or adjusted under 35 U.S.C. 154(b) by 0 days.

(21) Appl. No.: 14/113,907

(22) PCT Filed: Sep. 6, 2011

(86) PCT No.: PCT/CN2011/079372
§ 371 (c)(1),
(2), (4) Date: Oct. 25, 2013

(87) PCT Pub. No.: WO2013/020316
PCT Pub. Date: Feb. 14, 2013

(65) Prior Publication Data
US 2014/0142341 A1 May 22, 2014

(30) Foreign Application Priority Data
Aug. 8, 2011 (CN) .......................... 2011 1 0231786

(51) Int. Cl.
*C07C 209/48* (2006.01)
*C07C 209/62* (2006.01)
*C07C 211/36* (2006.01)

(52) U.S. Cl.
CPC ............. *C07C 209/62* (2013.01); *C07C 211/36* (2013.01); *C07C 209/48* (2013.01)
USPC ......................................................... 564/448

(58) Field of Classification Search
USPC ......................................................... 564/448
See application file for complete search history.

(56) References Cited

U.S. PATENT DOCUMENTS 5,756,845 A * 5/1998 Voit et al. ....................... 564/448
7,060,857 B2 * 6/2006 Funke et al. .................. 564/455
2010/0041921 A1 2/2010 Lettmann et al.

FOREIGN PATENT DOCUMENTS

| CN | 1483016 A | 3/2004 |
| CN | 101568516 A | 10/2009 |
| DE | 4010227 A1 | 10/1991 |
| DE | 19747913 C1 | 2/1999 |
| EP | 0394968 A1 | 10/1990 |
| EP | 0623585 A1 | 9/1994 |

OTHER PUBLICATIONS

International Search Report regarding PCT/CN2011/079372, dated Mar. 1, 2012.

* cited by examiner

*Primary Examiner* — Brian J Davis
(74) *Attorney, Agent, or Firm* — Armstrong Teasdale LLP

(57) ABSTRACT

Provided is a 3-aminomethyl-3,5,5-trimethylcyclohexylamine preparation method. A feeding flow of 3-cyano-3,5,5-trimethylcyclohexylamine is reacted with NH3 and hydrogen in the presence of a hydrogenation catalyst; the method is characterized by: firstly adding a basic compound to the feeding flow of 3-cyano-3,5,5-trimethylcyclohexylamine, and then after a portion of 3-cyano-3,5,5-trimethylcyclohexylamine has reacted, adding an acidic compound to reaction materials for further hydrogenation reaction to prepare the product. The method ensures that the aminonitrile content in the product is low, thus effectively reducing the duration of the reaction and greatly reducing the consumption of the catalyst during the hydrogenation reaction process.

28 Claims, 2 Drawing Sheets

3-AMINOMETHYL-3, 5, 5-TRIMETHYL CYCLOHEXYLAMINE PREPARATION METHOD

CROSS REFERENCE TO RELATED APPLICATIONS

This application claims priority to International Publication Number WO 2013/020316, filed on Sep. 6, 2011, and CN Patent Application No. 201110231786.4, filed on Aug. 8, 2011, the disclosures of which are hereby expressly incorporated by reference in their entireties.

FIELD OF INVENTION

The present invention relates to a method for preparing an aliphatic amine. Specifically, it relates to a method for preparing 3-aminomethyl-3,5,5-trimethylcyclohexylamine by hydrogenation of 3-cyano-3,5,5-trimethylcyclohexanone.

BACKGROUND OF THE INVENTION

3-Aminomethyl-3,5,5-trimethylcyclohexylamine (i.e., isophoronediamine, abbreviated as IPDA) is used as a starting material for preparing substances such as 3-isocyanatomethylene-3,5,5-trimethylcyclohexyl isocyanate (i.e., isophorone diisocyanate, abbreviated as IPDI) or polyamides, and also used as a curing agent for epoxy resins. 3-Aminomethyl-3,5,5-trimethylcyclohexylamine is prepared, on an industrial scale, by reacting 3-cyano-3,5,5-trimethylcyclohexanone (i.e., isophoronenitrile, abbreviated as IPN) with ammonia to form 3-cyano-3,5,5-trimethylcyclohexylamine (i.e., isophoronenitrilimine, abbreviated as IPNI), followed by a reductive amination reaction of IPNI with hydrogen in the presence of ammonia in a catalytic way. The above reaction processes are as follows:

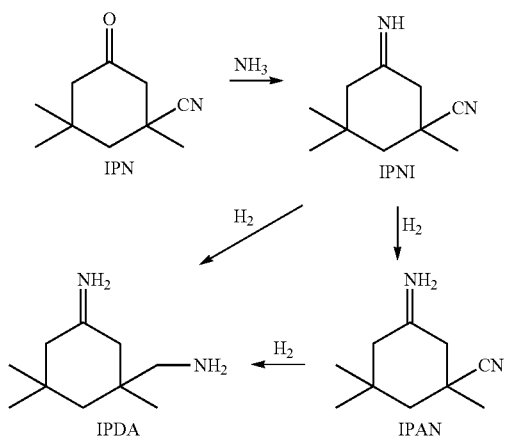

The reductive amination reaction can be carried out in multiple steps in order to improve the yield. EP-A1-0394968 discloses a process for the preparation of IPDA by multiple stages, wherein the imino group of IPNI is selectively hydrogenated, followed by a hydrogenation of the nitrile group under more drastic reaction conditions (at higher pressure and temperature). According to the disclosure in EP-A1-0394968, these reactions are carried out in such a manner as to reduce the reaction of forming 3-cyano-3,5,5-trimethyl cyclohexanol by the reduction of 3-cyano-3,5,5-trimethyl cyclohexanone which is in an equilibrium state with IPNI. However, the portion of other byproducts, such as cyclic compound, was 3-7% in the examples.

When the reductive amination reaction is carried out in the presence of basic catalyst(s) or basic compound(s), a high yield can be achieved. In the process disclosed by DE-A-4010227, the reductive amination reaction is partly carried out in the presence of the basic catalyst to obtain high yields.

In EP-A1-0623585, it is disclosed that doping the catalyst with basic components can lead to a higher yield in the reductive amination. DE-C-19747913 discloses a process for hydrogenating of imines and nitriles to form amines, especially the method of IPDA, wherein a quaternary ammonium hydroxide is added to improve the yield.

CN101568516A discloses a process for preparing IPDA by reacting a feeding flow containing 3-cyano-3,5,5-trimethylcyclohexylamine with hydrogen and ammonia in the presence of hydrogenation catalyst, which is characterized by that after a part of 3-cyano-3,5,5-trimethylcyclohexylamine has been reacted, the basicity of the reaction mixture is increased by contacting the resulting reaction mixture with a basic compound other than ammonia and/or with a basic catalyst during the subsequent reaction course. Although this method can improve the yield of isophorone diamine in the reaction product to a certain extent, the content of 3-cyano-3,5,5-trimethyl cyclohexylamine (i.e., aminonitrile, abbreviated as IPAN) is also relatively high in the products. One example thereof shows that a relatively high content of aminonitrile also exists in the reaction products having a relatively high yield of isophorone diamine (see Example 4, the yield of isophorone diamine is 98.4% and the aminonitrile content is 0.4%).

Aminonitrile is an intermediate product in the process for preparing IPDA and its boiling point is 255° C. The cis-isomer of IPDA has a boiling point of 253° C. and the trans-isomer one has a boiling point of 250° C. Due to their similar boiling points, it is difficult to separate aminonitrile from IPDA by using conventional means. Hence, in order to achieve better product quality, aminonitrile should be converted into IPDA as far as possible in the reaction process by hydrogenation.

Currently, there are the following defects in the existed methods of preparing IPDA: in order to make the aminonitrile content in the reaction products as low as possible, it is often required a hydrogenation reaction stage allowing for a longer residence time, which results in a large amount of the catalyst(s) needed in the hydrogenation reaction stage to make aminonitrile completely converted into IPDA by hydrogenation. However, using a large amount of the hydrogenation catalyst(s) means an increase in the catalyst cost together with an enlargement in the volume of the reactor and an increase in the investment of the reaction apparatus.

SUMMARY OF THE INVENTION

The object of the present invention is to provide a method for preparing 3-aminomethyl-3,5,5-trimethylcyclohexylamine. In the case of no loss occurring in the reaction yield, the method ensures that the aminonitrile content in the products is low, thus effectively shortening the residence time of the reaction and greatly reducing the consumption of the catalyst during the hydrogenation reaction stage, so as to overcome the defects existing in the prior art.

In order to achieve the above object, a technical solution of the present invention is provided as follows:

A method for preparing 3-aminomethyl-3,5,5-trimethyl-cyclohexylamine comprises the following steps:

a) reacting 3-cyano-3,5,5-trimethyl-cyclohexanone with $NH_3$ to obtain a product containing 3-cyano-3,5,5-trimethyl-cyclohexylamine;

b) mixing the product of step a) with a basic compound in the presence of hydrogen, $NH_3$ and a first hydrogenation catalyst to obtain a product containing 3-aminomethyl-3,5,5-trimethyl-cyclohexylamine and 3-cyano-3,5,5-trimethyl-cyclohexylamine, wherein the space velocity on the first hydrogenation catalyst is 0.5-10 g of 3-cyano-3,5,5-trimethyl-cyclohexanone/(per ml catalyst per hour), preferably 1-5 g of 3-cyano-3,5,5-trimethyl-cyclohexanone/(per ml catalyst per hour), more preferably 1.5-2 g of 3-cyano-3,5,5-trimethyl-cyclohexanone/(per ml catalyst per hour);

c) mixing the product of step b) with an acidic compound in the presence of hydrogen, $NH_3$ and a second hydrogenation catalyst, wherein the 3-cyano-3,5,5-trimethyl-cyclohexylamine in the products of step b) is converted into 3-aminomethyl-3,5,5-trimethyl-cyclohexylamine.

In the method according to the present invention, step a) is carried out at a temperature of 20-100° C. and a pressure of 0.5-30 MPa, preferably at a temperature of 20-70° C. and a pressure of 10-30 MPa, and more preferably at a temperature of 40-60° C. and a pressure of 10-30 MPa.

According to the method of the present invention, a catalyst may be or may not be used during the imidization reaction of 3-cyano-3,5,5-trimethyl-cyclohexanone with $NH_3$ in step a). If a catalyst is used in step a), the catalyst can be acidic metal oxides, inorganic ion-exchange resins or organic ion exchange resins, such as alumina, titania, zirconia, silica, zeolite and the like. The space velocity on the catalyst is 0.5-20 g of IPN/(per ml catalyst per hour), preferably 1-10 g of IPN/(per ml catalyst per hour), more preferably 2-6 g of IPN/(per ml catalyst per hour).

In step a), the molar ratio of $NH_3$ to 3-cyano-3,5,5-trimethyl-cyclohexanone is 5:1-200:1, preferably 10:1-100:1, and more preferably 20:1-80:1.

According to the method of the present invention, the imidization reaction of step a) may be carried out under a hydrogen atmosphere or without hydrogen. Preferably, the imidization reaction of step a) is carried out under a hydrogen atmosphere, wherein the molar ratio of hydrogen to IPN is 3:1-1000:1, preferably 4:1-500:1, more preferably 10:1-500:1, further preferably 15:1-300:1, and particularly preferably 20:1-100:1.

According to the method of the present invention, the imidization reaction of IPN can be carried out in the presence of a solvent, such as in alcohol or ether. The examples of the solvent include ethanol, butanol or tetrahydrofuran. Preferably, the imidization reaction of IPN is carried out in the absence of a solvent.

According to the method of the present invention, the imidization reaction of IPN is preferably carried out in a continuously manner. Usually, the imidization reaction of IPN is carried out in a pressure vessel which preferably is a tubular reactor. The tubular reactor may exist in a form of a fixed bed which is useful for the formation of the catalyst of imidization reaction. Preferably, a feeding flow of IPN and $NH_3$ enters into the bottom of the reactor and the materials are discharged from the top of the reactor. The materials of the imidization reaction generally contain IPNI, ammonia and unreacted IPN. The conversion of IPN into IPNI is usually 80% or more, even up to 90% or more, and the maximum is up to 95% or more.

According to the method of the present invention, the product of step b) mainly comprises IPDA and aminonitrile. Preferably, in the product of step b), the content of aminonitrile is 5-20 wt %, preferably 10-15 wt %.

In step b), suitable basic compounds include alkali metal compounds, such as oxides, hydroxides or carbonates of alkali metals, or oxides, hydroxides or carbonates of alkaline earth metals, or oxides, hydroxides or carbonates of rare earth metals; wherein oxides, hydroxides or carbonates of alkali metals, or oxides, hydroxides or carbonates of alkaline earth metals are preferable. More preferably, the basic compound may be $Li_2O$, $Na_2O$, $K_2O$, $Rb_2O$, $Cs_2O$, LiOH, NaOH, KOH, RbOH, CsOH, $Li_2CO_3$, $Na_2CO_3$, $K_2CO_3$, $Rb_2CO_3$, MgO, CaO, SrO, BaO, $Mg(OH)_2$, $Ca(OH)_2$, $Sr(OH)_2$, $Ba(OH)_2$, $MgCO_3$, $CaCO_3$, $SrCO_3$ or $BaCO_3$; and the most preferable one may be LiOH, NaOH or KOH.

According to the method of the present invention, the product of imidization reaction in step a) is mixed with the basic compound followed by carrying out step b), then the resulting mixture is introduced into the hydrogenation reactor. The mass ratio of the basic compound in step b) to 3-cyano-3,5,5-trimethyl-cyclohexanone in step a) is 1:100-1:1000. Preferably, the basic compound is used in the form of a solution, wherein the solvent can be water, alcohol or ether, etc. Preferably, the basic compound is used in the form of an alcohol solution of the basic compound, more preferably in the form of a methanol or ethanol solution of the basic compound. The concentration of the solution is 0.1-10 wt %, preferably 1-5 wt %.

Step b) is carried out at a temperature of 50-130° C. and a pressure of 10-30 MPa, preferably at a temperature of 60-100° C. and a pressure of 15-20 MPa. The molar ratio of $NH_3$ to IPN is 5:1-200:1, preferably 10:1-100:1, more preferably 20:1-80:1. Moreover, the molar ratio of hydrogen to IPN is 3:1-1000:1, preferably 4:1-500:1, more preferably 10:1-500:1, still more preferably 15:1-300:1, and particularly preferably 20:1-100:1. Hydrogen can be mixed with IPNI materials after the imidization reaction but before the hydrogenation reaction; or hydrogen can be mixed with IPN and $NH_3$ at the beginning.

In the method according to the present invention, suitable acidic compound of step c) is an organic acid. Preferably, the organic acid can be a C1-C40 organic monoacid, a $C_1$-$C_{40}$ organic diacid or a $C_1$-$C_{40}$ organic polyacid. More preferably, the organic acid can be a $C_1$-$C_{16}$ organic monoacid, a $C_1$-$C_{16}$ organic diacid or a $C_1$-$C_{16}$ organic polyacid. Still more preferably, the organic acid can be formic acid, acetic acid, methoxy acetic acid, propionic acid, caproic acid, lauric acid, benzoic acid, phthalic acid, phenylacetic acid, 2-ethylhexanoic acid, succinic acid, glutaric acid, adipic acid, or suberic acid; particularly preferably formic acid or acetic acid.

In the method according to the present invention, the mass ratio of the acidic compound in step c) to 3-cyano-3,5,5-trimethyl-cyclohexanone in step a) is 1:100-1:1000. The acidic compound is preferably used in the form of a solution, wherein the solvent can be water, alcohol or ether, etc. The acidic compound in an alcohol solution is preferable. More preferably, the acidic compound in methanol or ethanol solution is rather preferable. The concentration of the solution is 0.1-10 wt %, preferably 1-5 wt %.

Step c) is carried out at a temperature of 50-130° C. and a pressure of 10-30 MPa, preferably at a temperature of 100-130° C. and a pressure of 15-20 MPa. The space velocity on the catalyst is 0.5-20 g of IPN/(per ml catalyst per hour), preferably 0.5-15 g of IPN/(per ml catalyst per hour), and more preferably 5-15 g of IPN/(per ml catalyst per hour). The molar ratio of hydrogen in step c) to 3-cyano-3,5,5-trimethyl-cyclohexanone in step a) is 3:1-1000:1 and preferably 4:1-500:1, more preferably 10:1-500:1, still more preferably 15:1-300:1, and particularly preferably 20:1-100:1.

The first hydrogenation catalyst in step b) and the second hydrogenation catalyst in step c) may be the same or different. The catalyst used in the hydrogenation reaction is a hydrogenation catalyst having cobalt or nickel as the active component, such as supported cobalt/nickel catalyst or skeleton cobalt/nickel catalyst, preferably supported/skeleton cobalt catalyst, more preferably Raney cobalt.

According to the method of the present invention, the hydrogenation reactions in step b) and step c) are both carried out continuously in a pressure vessel, which can be for example, a hydrogenation reactor, preferably a tubular reactor, and more preferably a trickle-bed reactor. The hydrogenation reactor may be a thermostat reactor or a variable temperature reactor which can be for example, an adiabatic reactor.

3-Cyano-3,5,5-trimethyl-cyclohexylamine (i.e., aminonitrile) is a product of partial hydrogenating 3-cyano-3,5,5-trimethyl-cyclohexylamine. As the boiling point of aminonitrile is similar to that of IPDA, it is difficult to separate aminonitrile from IPDA by distillation or the like means. In order to improve the purity of IPDA, it is necessary to convert aminonitrile into IPDA by hydrogenation as far as possible in the reaction process. Usually, the amount of aminonitrile as an impurity presented in the purified IPDA is required to be less than 0.15 wt % or even lower.

It has been found in research that the introduction of additives, in particular the introduction of a basic compound, can be a great help to improve the hydrogenation reaction rate in the previous stage, particularly improve the hydrogenation rate of imine group greatly. However, the inventors have further found that the presence of a basic compound additive will be disadvantageous to the hydrogenating conversion of the remaining aminonitrile into IPDA after the overwhelming majority of aminonitrile is converted into IPDA, for example, after 80-90% of aminonitrile is converted into IPDA by hydrogenation. Moreover, the greater the concentration of the basic compound additive is, the more residence time the hydrogenating conversion of the remaining aminonitrile into IPDA needs.

The present inventors have surprisingly found in their research that the rate of hydrogenating conversion of the remaining aminonitrile into IPDA can be accelerated by addition of an acidic compound into the reaction mixture when the reaction product contains 5%-20% of aminonitrile, thereby reducing the amount of catalyst and shortening the residence time needed in the hydrogenation reaction of aminonitrile greatly. Moreover, the content of aminonitrile in the reaction products is only 0-0.15 wt %, usually less than 0.1 wt %, or even less than 0.05 wt %. The usage of the hydrogenation catalyst can be reduced to an amount which corresponds to 30-50 wt % of the usage of hydrogenation catalyst in existed processes, thereby reducing the size for the hydrogenation reactor, the reaction apparatus investment and the producing cost.

DETAILED DESCRIPTION OF THE INVENTION

Further illustration is made to the present invention through the following examples, while the present invention is not limited by them.

In the present invention, the quantitative analyses of 3-cyano-3,5,5-trimethyl-cyclohexylamine, 3-aminomethyl-3,5, 5-trimethyl-cyclohexylamine and aminonitrile are performed by gas chromatography, and the chromatographic analysis conditions are as follows:

Column: Agilent HP-5 (size: 30 m×0.32 mm×0.25 mm)

Inlet temperature: 280° C.

Split ratio: 30:1

Column flow rate: 1.5 ml/min

Column temperature: 100° C. 0.5 min;

increasing to 260° C. at a rate of 15° C./min, maintaining for 8 mins

Detector temperature: 280° C., $H_2$ flow rate: 35 ml/min

Air flow rate: 350 ml/min

Figure 1:
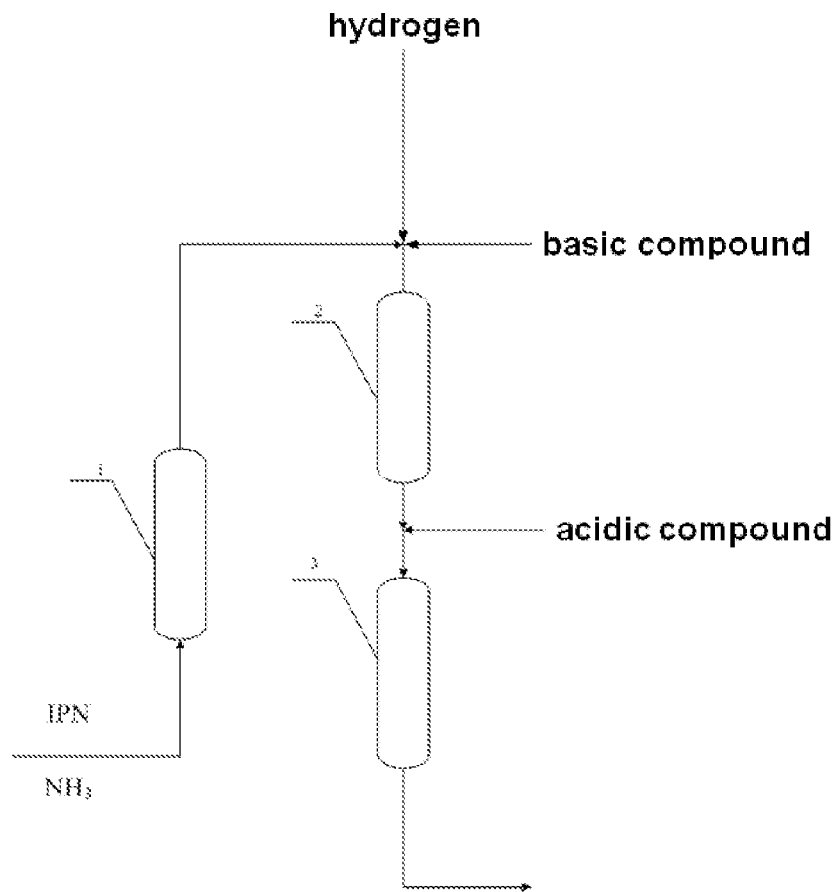
FIG. 1 is a schematic diagram according to one embodiment of the inventive method.

One embodiment of the inventive method is shown in FIG. 1. IPN and $NH_3$ were fed into the imidization reactor 1 in the presence of a catalyst. Then a basic compound together with hydrogen were introduced into the reaction materials, followed by the reaction materials being introduced into the first-stage hydrogenation reactor 2. The reaction materials were reacted in the presence of $NH_3$ and hydrogen as well as the hydrogenation catalyst. Subsequently, an acidic compound was added into the reaction materials, followed by the reaction materials being introduced into the second-stage hydrogenation reactor 3, and the reaction materials are reacted in the presence of $NH_3$ and hydrogen as well as the hydrogenation catalyst to obtain the final product, i.e., IPDA.

Figure 2:
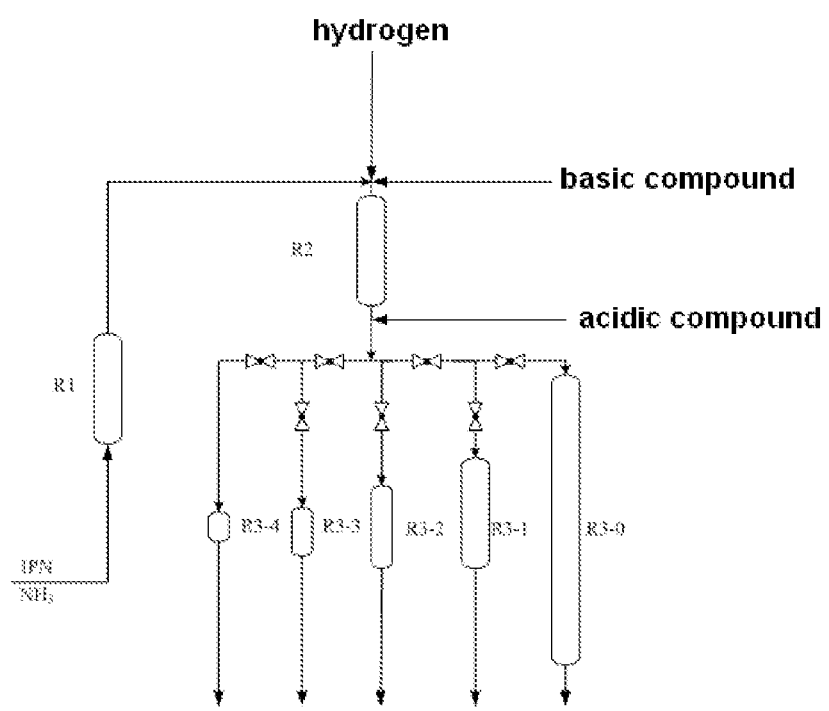
FIG. 2 is a schematic diagram according to another embodiment of the inventive method.

FIG. 2 illustrates the specific technological process of the following Examples and Comparative Examples. In FIG. 2, symbol R1 represents an imidization reactor which is a tubular reactor with an internal height of 75 mm and a diameter of 20 mm; symbol R2 represents a first-stage hydrogenation reactor which is a trickle bed reactor with an internal height of 150 mm and a diameter of 20 mm; and symbols R3-0, R3-1, R3-2, R3-3, and R3-4 respectively represent second-stage hydrogenation reactors with different volumes by means of trickle bed reactors. Specifically, Reactor R3-0 has an internal height of 450 mm and a diameter of 20 mm; Reactor R3-1 has an internal height of 150 mm and a diameter of 20 mm; Reactor R3-2 has an internal height of 120 mm and a diameter of 20 mm; Reactor R3-3 has an internal height of 60 mm and a diameter of 20 mm; and Reactor R3-4 has an internal height of 37.5 mm high and a diameter of 20 mm. When the test is conducted, only one of Reactors R3-0, R3-1, R3-2, R3-3 and R3-4 is used as the second-stage hydrogenation reactor.

Reactor R1 is filled with 23 ml of γ-Al2O3 spheres having a diameter of 0.5 mm. Reactors R2, R3-0, R3-1, R3-2, R3-3 and R3-4 were respectively filled with 47 ml, 141 ml, 47 ml, 37 ml, 18 ml, 11 ml of 16-30 mesh massive fixed bed Raney cobalt catalyst.

Comparative Example 1

Referring to the diagram as shown in FIG. 2, the temperature in Reactor R1 was controlled at 40° C., the temperature in Reactor R2 was controlled at 60° C., and the temperature in Reactor R3-0 was controlled at 130° C. The pressures in Reactors R1, R2, and R3-0 were all controlled at 15 MPa. The charging rate of IPN was 80 g/h. The charging rate of $NH_3$ was 168 g/h. The flow rate of hydrogen was 1100 N L/h. The reaction materials were introduced into Reactor R2, followed by a methanol solution of 5% NaOH in mass concentration being added into Reactor R2 in a charging rate of 16 g/h. The space velocities on each catalyst within each reactor were as follows:

| Reactor | Space Velocity on the Catalyst (g of IPN/(per ml catalyst per hour)) |
|---------|----------------------------------------------------------------------|
| R1      | 3.5                                                                  |
| R2      | 1.7                                                                  |
| R3-0    | 0.57                                                                 |

After the apparatus was operated for 100 hours, a sample was withdrawn from the outlet of Reactor R1 and analyzed by gas chromatography, wherein the content of 3-cyano-3,5,5-trimethyl-cyclohexylamine was 95%. Another sample was withdrawn from the outlet of Reactor R2 and analyzed by gas chromatography, wherein the content of IPDA was 80% and the content of aminonitrile was 15%. Still another sample was withdrawn from the outlet of Reactor R3-0 and analyzed by gas chromatography, wherein the content of IPDA was 97.9% and the content of aminonitrile was 0.14%.

Example 1

Referring to the diagram as shown in FIG. 2, the temperature in Reactor R1 was controlled at 40° C., the temperature in Reactor R2 was controlled at 60° C. and the temperature in Reactor R3-0 was controlled at 130° C. The pressures in Reactors R1, R2, and R3-0 were all controlled at 15 MPa. The charging rate of IPN was 80 g/h. The charging rate of $NH_3$ was 168 g/h. The flow rate of hydrogen was 1100 STAN L/h. The reaction materials were introduced into Reactor R2, followed by a methanol solution of 5% NaOH in mass concentration being added into Reactor R2 in a charging rate of 16 g/h. The space velocities on each catalyst within each reactor were as follows:

| Reactor | Space Velocity on the Catalyst (g of IPN/(per ml catalyst per hour)) |
|---------|----------------------------------------------------------------------|
| R1      | 3.5                                                                  |
| R2      | 1.7                                                                  |
| R3-0    | 0.57                                                                 |

After the apparatus was operated for 100 hours, a methanol solution of 5% formic acid in mass concentration was added into the reaction mixture in a charging rate of 16 g/h, followed by the reaction mixture being introduced into Reactor R3-0. After the apparatus was operated for 200 hours, a sample was drawn from the outlet of Reactor R1, wherein the content of 3-cyano-3,5,5-trimethyl-cyclohexylamine was 95%. Another sample was withdrawn from the outlet of Reactor R2 and analyzed by gas chromatography, wherein the content of IPDA was 80% and the content of aminonitrile was 15%. Still another sample was withdrawn from the outlet of Reactor R3-0 and analyzed by gas chromatography, wherein the content of IPDA was 98.5% and the content of aminonitrile was 0.01%.

It can be seen from the comparison between Example 1 and Comparative Example 1 that the aminonitrile content in the product can be effectively reduced by the addition of an acidic compound into the partially-hydrogenated imine-contain' reaction flow.

Example 2

Referring to the diagram as shown in FIG. 2, the temperature in Reactor R1 was controlled at 40° C., the temperature in Reactor R2 was controlled at 60° C. and the temperature in each of Reactors R3-0, R3-1, R3-2, R3-3 and R3-4 was controlled at 130° C. The pressures in each of Reactors R1, R2, R3-0, R3-1, R3-2, R3-3 and R3-4 were all controlled at 15 MPa. The charging rate of IPN was 80 g/h. The charging rate of $NH_3$ was 168 g/h, The flow rate of hydrogen was 1100 STAN L/h. A methanol solution of 5% NaOH in mass concentration was added into the reaction mixture in a charging rate of 16 followed by the reaction mixture being introduced into Reactor R2. A methanol solution of 5% formic acid ifs mass concentration was added into the reaction mixture in a charging rate of 16 g/h, followed by the reaction mixture being introduced into the second-stage hydrogenation reactor. The space velocities on each catalyst within each reactor were as follows:

| Reactor | Space Velocity on the Catalyst (g of IPN/(per ml catalyst per hour)) |
|---------|----------------------------------------------------------------------|
| R1      | 3.5                                                                  |
| R2      | 1.7                                                                  |
| R3-0    | 0.57                                                                 |
| R3-1    | 1.7                                                                  |
| R3-2    | 2.2                                                                  |
| R3-3    | 4.4                                                                  |
| R3-4    | 7.3                                                                  |

When the testing apparatus was operated for 300 hours, 400 hours, 500 hours, and 600 hours, the products of the first-stage hydrogenation reaction were switched to Reactors R3-1, R3-2, R3-3 and R3-4 respectively. After being switched for 50 hours, samples were withdrawn from the outlets of each of Reactors R3-1, R3-2, R3-3 and R3-4 respectively and analyzed by gas chromatography for determining the contents of IPDA and aminonitrile. The results are as shown in the following table:

TABLE 1

| Outlet of Reactor | Content of IPDA (wt) | Content of Aminonitrile (wt) |
|-------------------|----------------------|------------------------------|
| R3-1              | 98.6%                | 0.02%                        |
| R3-2              | 98.5%                | 0.03%                        |
| R3-3              | 98.5%                | 0.04%                        |
| R3-4              | 98.3%                | 0.14%                        |

It can be seen from the comparison between Example 2 and Comparative Example 1 that the catalyst amount required in the second-stage hydrogenation reaction can, by the addition of an acidic compound into the partially-hydrogenated product, be reduced to 1/12 of the catalyst amount required in the case that no acidic compound was added into the partially-hydrogenated product, provided that contents of aminonitrile in the final products of Example 2 and Comparative Example 1 were the same.

Example 3

The temperature in Reactor R1 was controlled at 60° C., the temperature in Reactor R2 was controlled at 100° C., and the temperature in Reactor R3-0 was controlled at 100° C. The pressures in Reactors R1, R2, and R3-0 were all controlled at 20 MPa. The charging rate of IPN was 80 g/h. The charging rate of $NH_3$ was 650 g/h. The flow rate of hydrogen was 220 STAN L/h. A dimethyl ether solution of 1% LiOH in mass concentration was added into the reaction mixture in a charging rate of 8 g/h, followed by the reaction mixture being introduced into Reactor R2. An aqueous solution of 1% phthalic acid in mass concentration was added into the reaction mixture in a charging rate of 8 g/h, followed by the reaction mixture being introduced into Reactor R3-0.

After the apparatus was operated for 100 hours, a sample was withdrawn from the outlet of Reactor R1 and analyzed by gas chromatography, wherein the content of 3-cyano-3,5,5-trimethyl-cyclohexylamine was 94%. Another sample was withdrawn from the outlet of Reactor R2 and analyzed by gas chromatography, wherein the content of IPDA was 81% and the content of aminonitrile was 14.5%.

When the test started, Reactor R3-0 was used as the second-stage hydrogenation reactor. After the reaction was performed for 200 hours, 300 hours, 400 hours, and 500 hours, Reactors R3-1, R3-2, R3-3 and R3-4 were switched to as the second-stage hydrogenation reactors, respectively.

The space velocities on each catalyst within each reactor were as follows:

| Reactor | Space Velocity on the Catalyst (g of IPN/(per ml catalyst per hour)) |
|---|---|
| R1 | 3.5 |
| R2 | 1.7 |
| R3-0 | 0.57 |
| R3-1 | 1.7 |
| R3-2 | 2.2 |
| R3-3 | 4.4 |
| R3-4 | 7.3 |

After Reactor R3-0 was operated for 50 hours, as well as after finishing the switch for 50 hours, samples were withdrawn from the outlets of the corresponding Reactors and were analyzed the contents of IPDA and aminonitrile thereof. The results are as shown in the following table:

TABLE 2

| Outlet of Reactor | Content of IPDA (wt) | Content of Aminonitrile (wt) |
|---|---|---|
| R3-0 | 98.7% | 0% |
| R3-1 | 98.7% | 0.01% |
| R3-2 | 98.6% | 0.02% |
| R3-3 | 98.6% | 0.03% |
| R3-4 | 98.4% | 0.15% |

Example 4

The temperature in Reactor R1 was controlled at 50° C., the temperature in Reactor R2 was controlled at 80° C., and the temperature in Reactor R3-0 was controlled at 115° C. The pressures in Reactors R1, R2, and R3-0 were all controlled at 18 MPa. The charging rate of IPN was 80 g/h. The charging rate of $NH_3$ was 344 g/h. The flow rate of hydrogen was 550 STAN L/h. An aqueous solution of 2.5% $K_2CO_3$ in mass concentration was added into the reaction mixture in a charging rate of 16 g/h, followed by the reaction mixture being introduced into Reactor R2. A THF solution of 2.5% lauric acid in mass concentration was added into the reaction mixture in a charging rate of 16 g/h, followed by the reaction mixture being introduced into Reactor R3-0.

After the apparatus was operated for 100 hours, a sample was withdrawn from the outlet of Reactor R1 and analyzed by gas chromatography, wherein the content of 3-cyano-3,5,5-trimethyl-cyclohexylamine was 96%. Another sample was withdrawn from the outlet of Reactor R2 and analyzed by gas chromatography, wherein the content of IPDA was 82.5% and the content of aminonitrile was 13.5%.

When the test started, Reactor R3-0 was used as the second-stage hydrogenation reactor. After the reaction was performed for 200 hours, 300 hours, 400 hours, and 500 hours, Reactors R3-1, R3-2, R3-3 and R3-4 were switched to as the second-stage hydrogenation reactors, respectively.

The space velocities on each catalyst within each reactor were as follows:

| Reactor | Space Velocity on the Catalyst (g of IPN/(per ml catalyst per hour)) |
|---|---|
| R1 | 3.5 |
| R2 | 1.7 |
| R3-0 | 0.57 |
| R3-1 | 1.7 |
| R3-2 | 2.2 |
| R3-3 | 4.4 |
| R3-4 | 7.3 |

After Reactor R3-0 was operated for 50 hours, as well as after finishing the switch for 50 hours, samples were withdrawn from the outlets of the corresponding Reactors and were analyzed the contents of IPDA and aminonitrile thereof. The results are as shown in the following table:

TABLE 3

| Outlet of Reactor | Content of IPDA (wt) | Content of Aminonitrile (wt) |
|---|---|---|
| R3-0 | 99.0% | 0% |
| R3-1 | 99.0% | 0.02% |
| R3-2 | 98.9% | 0.02% |
| R3-3 | 98.8% | 0.05% |
| R3-4 | 98.6% | 0.14% |

Example 5

The temperature in Reactor R1 was controlled at 80° C., the temperature in Reactor R2 was controlled at 110° C., and the temperature in Reactor R3-0 was controlled at 120° C. The pressures in Reactors R1, R2, and R3-0 were all controlled at 20 MPa. The charging rate of IPN was 160 g/h. The charging rate of $NH_3$ was 344 g/h. The flow rate of hydrogen was 1000 STAN L/h. An ethanol solution of 4% LiOH in mass concentration was added into the reaction mixture in a charging rate of 16 g/h, followed by the reaction mixture being introduced into Reactor R2. An ethanol solution of 2.5% acetic acid in mass concentration was added into the reaction mixture in a charging rate of 8 g/h, followed by the reaction mixture being introduced into Reactor R3-0.

After the apparatus was operated for 100 hours, a sample was withdrawn from the outlet of Reactor R1 and analyzed by gas chromatography, wherein the content of 3-cyano-3,5,5-trimethyl-cyclohexylamine was 93%. Another sample was withdrawn from the outlet of Reactor R2 and analyzed by gas chromatography, wherein the content of IPDA was 79.5% and the content of aminonitrile was 19.5%.

When the test started, Reactor R3-0 was used as the second-stage hydrogenation reactor. After the reaction was performed for 200 hours, 300 hours, 400 hours, and 500 hours, Reactors R3-1, R3-2, R3-3 and R3-4 were switched to as the second-stage hydrogenation reactors, respectively.

The space velocities on each catalyst within each reactor were as follows:

| Reactor | Space Velocity on the Catalyst (g of IPN/(per ml catalyst per hour)) |
|---|---|
| R1 | 7.0 |
| R2 | 3.4 |
| R3-0 | 1.1 |
| R3-1 | 3.4 |
| R3-2 | 4.3 |
| R3-3 | 8.9 |
| R3-4 | 14.5 |

After Reactor R3-0 was operated for 50 hours, as well as after finishing the switch for 50 hours, samples were withdrawn from the outlets of the corresponding Reactors and were analyzed the contents of IPDA and aminonitrile thereof. The results are as shown in the following table:

TABLE 4

| Outlet of Reactor | Content of IPDA (wt) | Content of Aminonitrile (wt) |
|---|---|---|
| R3-0 | 97.9% | 0% |
| R3-1 | 97.9% | 0.02% |
| R3-2 | 98.1% | 0.02% |
| R3-3 | 97.8% | 0.05% |
| R3-4 | 97.6% | 0.14% |

The invention claimed is:

1. A method for preparing 3-aminomethyl-3,5,5-trimethylcyclohexylamine, the method comprising:
    a) reacting 3-cyano-3,5,5-trimethyl-cyclohexanone with $NH_3$ to obtain a product containing 3-cyano-3,5,5-trimethyl-cyclohexylamine;
    b) mixing the product of step a) with a basic compound in the presence of hydrogen, $NH_3$ and a first hydrogenation catalyst to obtain a product containing 3-aminomethyl-3,5,5-trimethylcyclohexylamine and 3-cyano-3,5,5-trimethyl-cyclohexylamine, wherein the space velocity on the first hydrogenation catalyst is 0.5-10 g of 3-cyano-3,5,5-trimethyl-cyclohexanone/(per ml catalyst per hour);
    c) mixing the product of step b) with an acidic compound in the presence of hydrogen, $NH_3$ and a second hydrogenation catalyst, wherein the 3-cyano-3,5,5-trimethyl-cyclohexylamine in the product of step b) is converted into 3-aminomethyl-3,5,5-trimethyl-cyclohexylamine.

2. The method according to claim 1, wherein the content of 3-cyano-3,5,5-trimethyl-cyclohexylamine in the product of step b) is 5-20 wt %.

3. The method according to claim 2, wherein the acidic compound in step c) is an organic acid.

4. The method according to claim 3, wherein the mass ratio of the acidic compound in step c) to 3-cyano-3,5,5-trimethyl-cyclohexanone in step a) is 1:100-1:1000.

5. The method according to claim 4, wherein the acidic compound of step c) is in the form of a solution of the acidic compound, wherein the solvent is water, alcohol or ether; and the concentration of the solution is 0.1-10 wt %.

6. The method according to 1, wherein the basic compound of step b) is alkali metal compounds.

7. The method according to claim 1, wherein the mass ratio of the basic compound in step b) to 3-cyano-3,5,5-trimethyl-cyclohexanone in step a) is 1:100-1:1000.

8. The method according to claim 1, wherein the basic compound of step b) is in the form of a solution of the basic compound, wherein the solvent is water, alcohol or ether; and the concentration of the solution is 0.1-10 wt %.

9. The method according to claim 1, wherein step a) is carried out at a temperature of 20-100° C. and a pressure of 0.5-30 MPa; step b) is carried out at a temperature of 50-130° C. and a pressure of 10-30 MPa; and step c) is carried out at a temperature of 50-130° C. and a pressure of 10-30 MPa.

10. The method according to claim 1, wherein the space velocity on the catalyst in step c) is 0.5-20 g of 3-cyano-3,5,5-trimethyl-cyclohexanone/(per ml catalyst per hour).

11. The method according to claim 1, wherein step a) is carried out in the presence of a catalyst which is an acidic metal oxide, an inorganic ion-exchange resin or an organic ion exchange resin; and the space velocity on the catalyst is 0.5-20 g of 3-cyano-3,5,5-trimethylcyclohexanone/(per ml catalyst per hour).

12. The method according to claim 1, wherein the first hydrogenation catalyst in step b) and the second hydrogenation catalyst in step c) are the same or different, and the first hydrogenation catalyst and the second hydrogenation catalyst are independently hydrogenation catalysts having cobalt or nickel as the active component.

13. The method according to claim 1, wherein the molar ratio of $NH_3$ in step a) and step b) to 3-cyano-3,5,5-trimethyl-cyclohexanone is 5:1-200:1; and the molar ratio of hydrogen in step b) and step c) to 3-cyano-3,5,5-trimethyl-cyclohexanone is 3:1-1000:1.

14. The method according to claim 1, wherein step a) is carried out in the presence of hydrogen, and the molar ratio of the hydrogen to 3-cyano-3,5,5-trimethyl-cyclohexanone is 3:1-1000:1.

15. The method according to claim 1, wherein step b) and step c) are carried out in a hydrogenation reactor.

16. A method for preparing 3-aminomethyl-3,5,5-trimethyl-cyclohexylamine, the method comprising:
    a) reacting 3-cyano-3,5,5-trimethyl-cyclohexanone with $NH_3$ to obtain a product containing 3-cyano-3,5,5-trimethyl-cyclohexylamine;
    b) mixing the product of step a) with a basic compound in the presence of hydrogen, $NH_3$ and a first hydrogenation catalyst to obtain a product containing 3-aminomethyl-3,5,5-trimethylcyclohexylamine and 3-cyano-3,5,5-trimethyl-cyclohexylamine, wherein the space velocity on the first hydrogenation catalyst is 0.5-10 g of 3-cyano-3,5,5-trimethyl-cyclohexanone/(per ml catalyst per hour);
    c) mixing the product of step b) with an acidic compound in the presence of hydrogen, $NH_3$ and a second hydrogenation catalyst, wherein the 3-cyano-3,5,5-trimethyl-cyclohexylamine in the product of step b) is converted into 3-aminomethyl-3,5,5-trimethyl-cyclohexylamine;
    wherein the content of 3-cyano-3,5,5-trimethyl-cyclohexylamine in the product of step b) is 5-20 wt %;
    wherein the acidic compound in step c) is an organic acid; and
    wherein the space velocity on the catalyst in step c) is 0.5-20 g of 3-cyano-3,5,5-trimethylcyclohexanone/(per ml catalyst per hour).

17. The method according to claim 16, wherein the mass ratio of the acidic compound in step c) to 3-cyano-3,5,5-trimethyl-cyclohexanone in step a) is 1:100-1:1000; wherein the acidic compound of step c) is in the form of a solution of the acidic compound, wherein the solvent is water, alcohol or ether; and the concentration of the solution is 0.1-10 wt %.

18. A method for preparing 3-aminomethyl-3,5,5-trimethyl-cyclohexylamine, the method comprising:
  a) reacting 3-cyano-3,5,5-trimethyl-cyclohexanone with $NH_3$ to obtain a product containing 3-cyano-3,5,5-trimethyl-cyclohexylamine;
  b) mixing the product of step a) with a basic compound in the presence of hydrogen; $NH_3$ and a first hydrogenation catalyst to obtain a product containing 3-aminomethyl-3,5,5-trimethylcyclohexylamine and 3-cyano-3,5,5-trimethyl-cyclohexylamine, wherein the space velocity on the first hydrogenation catalyst is 0.5-10 g of 3-cyano-3,5,5-trimethyl-cyclohexanone/(per ml catalyst per hour);
  c) mixing the product of step b) with an acidic compound in the presence of hydrogen, $NH_3$ and a second hydrogenation catalyst, wherein the 3-cyano-3,5,5-trimethyl-cyclohexylamine in the product of step b) is converted into 3-aminomethyl-3,5,5-trimethyl-cyclohexylamine;
  wherein the content of 3-cyano-3,5,5-trimethyl-cyclohexylamine in the product of step b) is 5-20 wt %;
  wherein the acidic compound in step c) is an organic acid;
  wherein the space velocity on the catalyst in step c) is 0.5-20 g of 3-cyano-3,5,5-trimethylcyclohexanone/(per ml catalyst per hour); and
  wherein step b) and step c) are carried out in a hydrogenation reactor.

19. The method according to claim 18, wherein the mass ratio of the acidic compound in step c) to 3-cyano-3,5,5-trimethyl-cyclohexanone in step a) is 1:100-1:1000.

20. The method according to claim 19, wherein the acidic compound of step c) is in the form of a solution of the acidic compound, wherein the solvent is water, alcohol or ether; and the concentration of the solution is 0.1-10 wt %.

21. The method according to claim 3, wherein the organic acid is selected from the group consisting of a C1-C40 organic monoacid, a C1-C40 organic diacid, and a C1-C40 organic polyacid.

22. The method according to claim 21, wherein the organic acid is selected from the group consisting of formic acid, acetic acid, methoxy acetic acid, propionic acid, caproic acid, lauric acid, benzoic acid, phthalic acid, phenylacetic acid, 2-ethylhexanoic acid, succinic acid, glutaric acid, adipic acid, and suberic acid.

23. The method according to claim 5, wherein the solvent of the solution of the acidic compound of step c) is methanol or ethanol.

24. The method according to claim 6, wherein the basic compound of step b) is selected from the group consisting of oxides, hydroxides or carbonates of alkali metals, oxides, hydroxides or carbonates of alkaline earth metals, and oxides, hydroxides or carbonates of a rare earth metals.

25. The method according to claim 16, wherein the space velocity on the first hydrogenation catalyst in the step b) is 1-5 g of 3-cyano-3,5,5-trimethyl-cyclohexanone/(per ml catalyst per hour); the content of 3-cyano-3,5,5-trimethyl-cyclohexylamine in the product of step b) is 10-15 wt %; the acidic compound in step c) is selected from the group consisting of a C1-C40 organic monoacid, a C1-C40 organic diacid, and a C1-C40 organic polyacid; the space velocity on the catalyst in step c) is 0.5-15 g of 3-cyano-3,5,5-trimethyl-cyclohexanone/(per ml catalyst per hour).

26. The method according to claim 25, wherein the acidic compound in step c) is selected from the group consisting of formic acid, acetic acid, methoxy acetic acid, propionic acid, caproic acid, lauric acid, benzoic acid, phthalic acid, phenylacetic acid, 2-ethylhexanoic acid, succinic acid, glutaric acid, adipic acid, and suberic acid.

27. The method according to claim 18, wherein the space velocity on the first hydrogenation catalyst in the step b) is 1-5 g of 3-cyano-3,5,5-trimethyl-cyclohexanone/(per ml catalyst per hour); the content of 3-cyano-3,5,5-trimethyl-cyclohexylamine in the product of step b) is 10-15 wt %; the acidic compound in step c) is selected from the group consisting of a C1-C40 organic monoacid, a C1-C40 organic diacid, and a C1-C40 organic polyacid; the space velocity on the catalyst in step c) is 0.5-15 g of 3-cyano-3,5,5-trimethyl-cyclohexanone/(per ml catalyst per hour); step b) and step c) are carried out in a tubular reactor.

28. The method according to claim 27, wherein the acidic compound in step c) is selected from the group consisting of formic acid, acetic acid, methoxy acetic acid, propionic acid, caproic acid, lauric acid, benzoic acid, phthalic acid, phenylacetic acid, 2-ethylhexanoic acid, succinic acid, glutaric acid, adipic acid, and suberic acid.

* * * * *